(12) United States Patent
Brukilacchio (10) Patent No.: US 8,403,527 B2
(45) Date of Patent: Mar. 26, 2013

(54) LIGHT EMITTING DIODE PROJECTOR

(76) Inventor: Thomas J. Brukilacchio, Reading, MA (US)

( * ) Notice: Subject to any disclaimer, the term of this patent is extended or adjusted under 35 U.S.C. 154(b) by 0 days.

(21) Appl. No.: 13/274,932

(22) Filed: Oct. 17, 2011

(65) Prior Publication Data

US 2012/0099308 A1    Apr. 26, 2012

Related U.S. Application Data

(60) Provisional application No. 61/406,962, filed on Oct. 26, 2010.

(51) Int. Cl.
*F21V 1/00* (2006.01)

(52) U.S. Cl. ........ 362/235; 362/540; 362/305; 362/294; 362/244

(58) Field of Classification Search .................. 362/235, 362/540, 487, 542, 545, 326, 244, 305, 294
See application file for complete search history.

(56) References Cited

U.S. PATENT DOCUMENTS

| | | | |
|---|---|---|---|
| 4,915,479 A | 4/1990 | Clarke | |
| 5,146,248 A | 9/1992 | Duwaer | |
| 6,205,998 B1 | 3/2001 | Winston | |
| 6,272,269 B1 | 8/2001 | Naum | |
| 6,318,863 B1 | 11/2001 | Tiao et al. | |
| 6,967,986 B2 | 11/2005 | Kowarz et al. | |
| 6,968,103 B1 | 11/2005 | Schroll et al. | |
| 7,001,084 B2 | 2/2006 | Carpenter et al. | |
| 7,234,820 B2 | 6/2007 | Harbers et al. | |
| 7,455,410 B2 | 11/2008 | Furusawa et al. | |
| 7,481,538 B2 | 1/2009 | Furusawa et al. | |
| 2002/0114168 A1 | 8/2002 | Pelka et al. | |
| 2004/0022071 A1 | 2/2004 | Cheng et al. | |
| 2004/0218390 A1 | 11/2004 | Holman et al. | |
| 2005/0169579 A1 | 8/2005 | Temkin et al. | |
| 2005/0224846 A1 | 10/2005 | Imato et al. | |
| 2005/0243570 A1 | 11/2005 | Chaves et al. | |
| 2005/0275819 A1 | 12/2005 | Tolbert et al. | |
| 2006/0043400 A1 | 3/2006 | Erchak et al. | |
| 2007/0206390 A1 | 9/2007 | Brukilacchio et al. | |
| 2008/0192477 A1 | 8/2008 | Holder et al. | |
| 2008/0205034 A1 | 8/2008 | Kunkel et al. | |
| 2009/0073698 A1 | 3/2009 | Tatsuno | |
| 2009/0122533 A1 | 5/2009 | Brukilacchio | |

FOREIGN PATENT DOCUMENTS

KR    10-2010-011644 A    10/2010

OTHER PUBLICATIONS

Welford, W.T. and Winston, R.,"High Collection Nonimaging Optics", Academic Press, pp. 213-215.
PCT/US2011/001783 Search Report and Written Opinion Mailed on Oct. 12, 2011.

*Primary Examiner* — Joseph L Williams
(74) *Attorney, Agent, or Firm* — Francis J. Caufield (57) ABSTRACT

The invention relates to a light emitting diode (LED) light source comprising an LED die, or a closely packed die array or matrix of die arrays, substantially and efficiently coupled to non-imaging collection optics. The non-imaging collection optics operate to provide a homogenized LED output having a near field whose intensity is highly uniform and a reduced far field extent substantially preserving the étendue (area, solid angle, index squared product) of the LED output. The near field, in turn, is imaged by a downstream relay lens to an illumination plane a specific distance away.

25 Claims, 11 Drawing Sheets

LIGHT EMITTING DIODE PROJECTOR

CROSS REFERENCE TO RELATED APPLICATION

This application claims the benefit of priority from U.S. Provisional Patent Application No. 61/406,962 entitled LIGHT EMITTING DIODE PROJECTOR which was filed on Oct. 26, 2010 in the name of Thomas J. Brukilacchio, the entire contents of which are incorporated herein by reference.

FIELD OF THE INVENTION

This invention generally relates to the uniform projection of the emission from light emitting diodes (LEDs) onto a plane a finite distance from the emitting aperture for use in applications requiring high intensity uniform illumination over the spectral range including ultraviolet (UV) to mid infrared (MIR). Applications include industrial illumination such as machine vision, medical such as tissue illumination or fluorescence, biological such as illumination to aid in the growth of algae in well plates or as a multi-spectral illumination source for fluorescence excitation and subsequent detection by a camera imaging system.

BACKGROUND OF THE INVENTION

Current products requiring high intensity uniform illumination over the spectral range including ultraviolet (UV) to mid infrared (MIR) are based primarily on mercury arc lamps, which are expensive, inefficient, contain toxic materials dangerous to the environment, short lived, and operated by costly and high voltage ballasts. Xenon and metal halide short arc lamps have also been used, as have tungsten halogen sources.

As with mercury arc lamps, both xenon and metal halide lamps also contain toxic materials, expensive power supplies and ballasts and suffer from short lifetimes, requiring frequent replacement, interruptions in progress, and additional costs associated with both the labor for replacement and the lamp itself. A further disadvantage of tungsten halogen based systems is the relatively low output particularly for short blue and UV wavelengths.

The industry standard in both medical and industrial markets for providing high flux in the UVA band (extending from about 315 to 400 nm) optical radiation has been the mercury arc lamp. Mercury arc lamps are characterized by relatively narrow line spectra which in the UVA region is dominated by the i-line centered near 365 nm. Now, the fact that there are many mercury lines excited simultaneously between the deep UV and through the visible spectrum, means that much of the energy used to power the lamp is not going into this UV band which must be selected by using interference filters to extinguish the unwanted spectral components. Additional issues with the use of these high power mercury, xenon, and metal halide arc lamps include the undesirable affect of the arc moving around with time, resulting in flicker or instability in the intensity. Further, the fact that the arc moves requires an optical system with an effectively larger input aperture which reduces the maximum obtainable power density down stream in the optical system. Additionally, very large voltages are required from power supply ballasts on the order of kilovolts to start the lamps. These high voltages can damage sensitive medical and industrial instrumentation due to the emitted electromagnetic pulse. In addition to these issues with the use of mercury, xenon, and metal halide lamps, recent concern over the use of highly toxic materials has fueled the search for alternatives to the arc lamps and improvements over the low output and poor lifetime of tungsten based lamps.

It is a principle object of the present invention to provide an LED based projector system that replaces expensive toxic mercury based lamps where the LED based system is from 200% to 500% more efficient and >10× the lifetime relative to mercury lamps.

It is another object of the present invention to provide an LED based illumination system that operates at low voltage with no need for expensive and dangerous voltages required for the mercury based systems.

It is yet another object of the present invention to provide an LED based "Chip-on-Board" (COB) high power, high density LED die arrays in combination with unique non-imaging collection and imaging relay optics to provide a new generation of UV, Visible, and Mid Infrared LED projection systems as alternatives to toxic, short lived and energy inefficient mercury, xenon, metal halide and tungsten halogen lamp systems.

It is yet another object of the present invention to provide an LED projector that combines a very low thermal impedance "Chip-on-Board" (COB) LED die attachment technology with thermal impedance well under 1° C./W which is several times lower than conventional high performance high power LED prepackaged emitters. The use of such a low thermal impedance technology allows the current density to be increased substantially resulting in much higher optical power density and lower junction temperatures which translates into longer LED die lifetimes. Additionally, the warm up time for mercury, xenon and metal halide lamp systems is relatively long and they can not be pulsed on an off effectively. The much faster response time of LEDs allows a further reduction in energy usage as the LED based systems can be switched on and off where the arc lamp systems generally need to be operated continuously and switched on and off by use of mechanical shutters. Thus, the effective energy usage is even higher in practice for LEDs, depending on the duty cycle of the particular process in question.

Other objects of the invention will, in part, be obvious and, in part, appear hereinafter when the following detailed description is read in connection with the accompanying drawings.

SUMMARY OF THE INVENTION

This invention relates to a Light Emitting Diode (LED) based apparatus for providing high uniformity and power density area illumination in the Ultraviolet (UV) through the Mid Infrared spectrum for use in multispectral illumination and imaging, plant growth, broad spectral band solar simulation, medical fluorescence diagnostic imaging or industrial UV curing applications.

The invention herein describes a light emitting diode (LED) light source comprising an LED die or a closely packed die array or matrix of die arrays substantially and efficiently coupled to non-imaging collection optics which act to homogenize the LED output providing at the non-imaging collection optics exit aperture a high degree of near field intensity uniformity and a reduced far field extent substantially preserving the étendue (area, solid angle, index squared product) at the LED output. The near field, at the output of the collection optics, in turn, is imaged by a relay lens to an illumination plane a specific distance away. This projector provides a solid state light source of much improved stability, lifetime, illumination plane intensity uniformity, reduction of toxic materials, and specific spectral content required by today's most demanding industrial, medical, biological, and commercial illumination source applications relative to mercury, xenon, metal halide, and tungsten based lamp systems.

The primary components of the LED projector system include a high thermal conductivity LED COB board, direct attached LED die and wire bonds, a high collection efficiency non-imaging optic to collect and homogenize the LED emission, and an adjustable focus imaging lens system to relay the LED output to the illumination plane. The output aperture of the collection optic can include various apertures or spectral filters to modify the output of the light at the illumination plane. Alternatively, a zoom lens system could be used to change the magnification to achieve an adjustable illumination pattern size at a specific image distance. This LED based projector technology opens up new applications that were not previously either technically feasible, cost feasible or both.

BRIEF DESCRIPTION OF THE DRAWINGS

The structure, operation, and methodology of the invention, together with other objects and advantages thereof, may best be understood by reading the following detailed description in connection with the drawings in which each part has an assigned numeral or label that identifies it wherever it appears in the various drawings and wherein.

DETAILED DESCRIPTION

The present invention relates to Light Emitting Diode (LED) projection systems. The emission from an LED die or die array attached to a high thermal conductivity substrate is collected by a non-imaging optic and subsequently re-imaged by a system of lenses to the illumination plane some distance from the output aperture of the lens system. The LED board is in turn thermally coupled to a heat sink typically cooled by a fan or other air or water supply. The projector can illuminate a well defined area with the high uniformity and control over the spectrum and intensity pattern required of high performance industrial, medical, and biological illumination and image detection systems. Recently the advent of high brightness LEDs has enabled such projection systems to replace short arc mercury, xenon, and metal halide lamps as well as tungsten halogen. This has led to significant improvements in light stability, spectral control, lifetime, and energy efficiency afforded by the use of LEDs.

Figure 1:
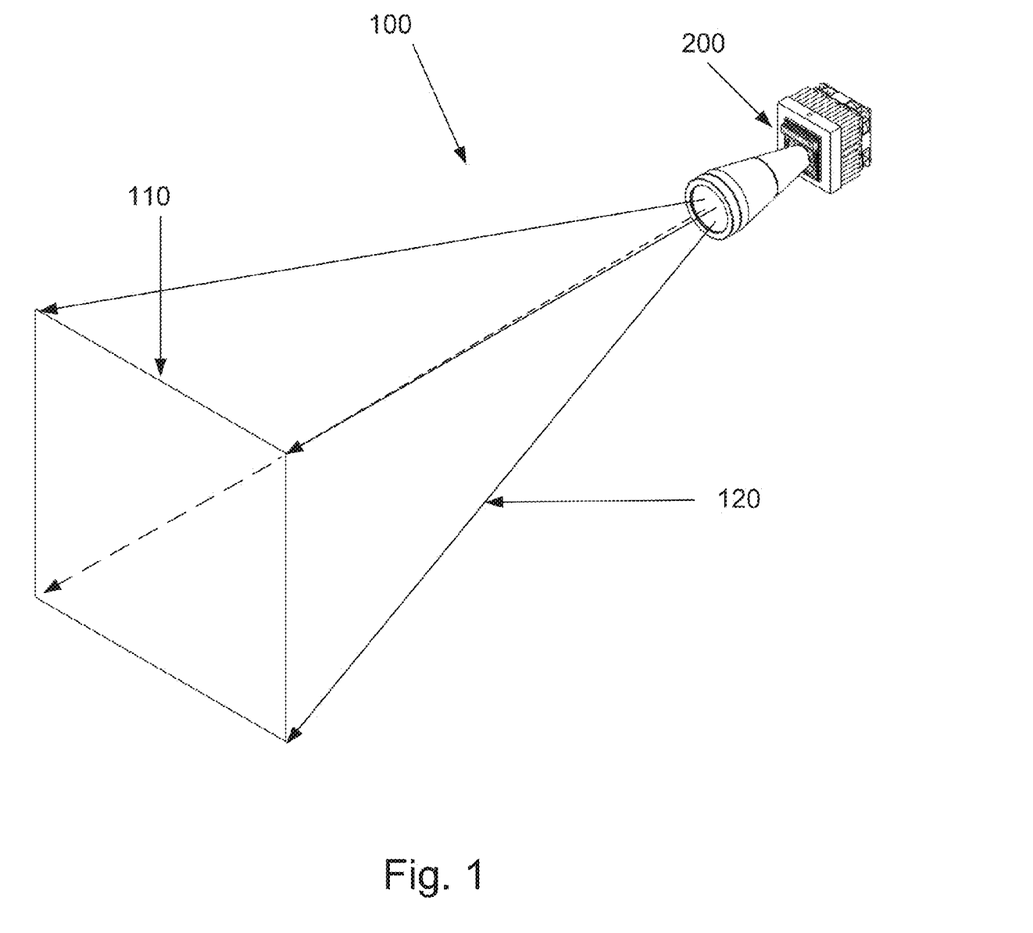
FIG. 1 shows a diagrammatic isometric view of a preferred embodiment of the projector system of the invention.
Figure 2:
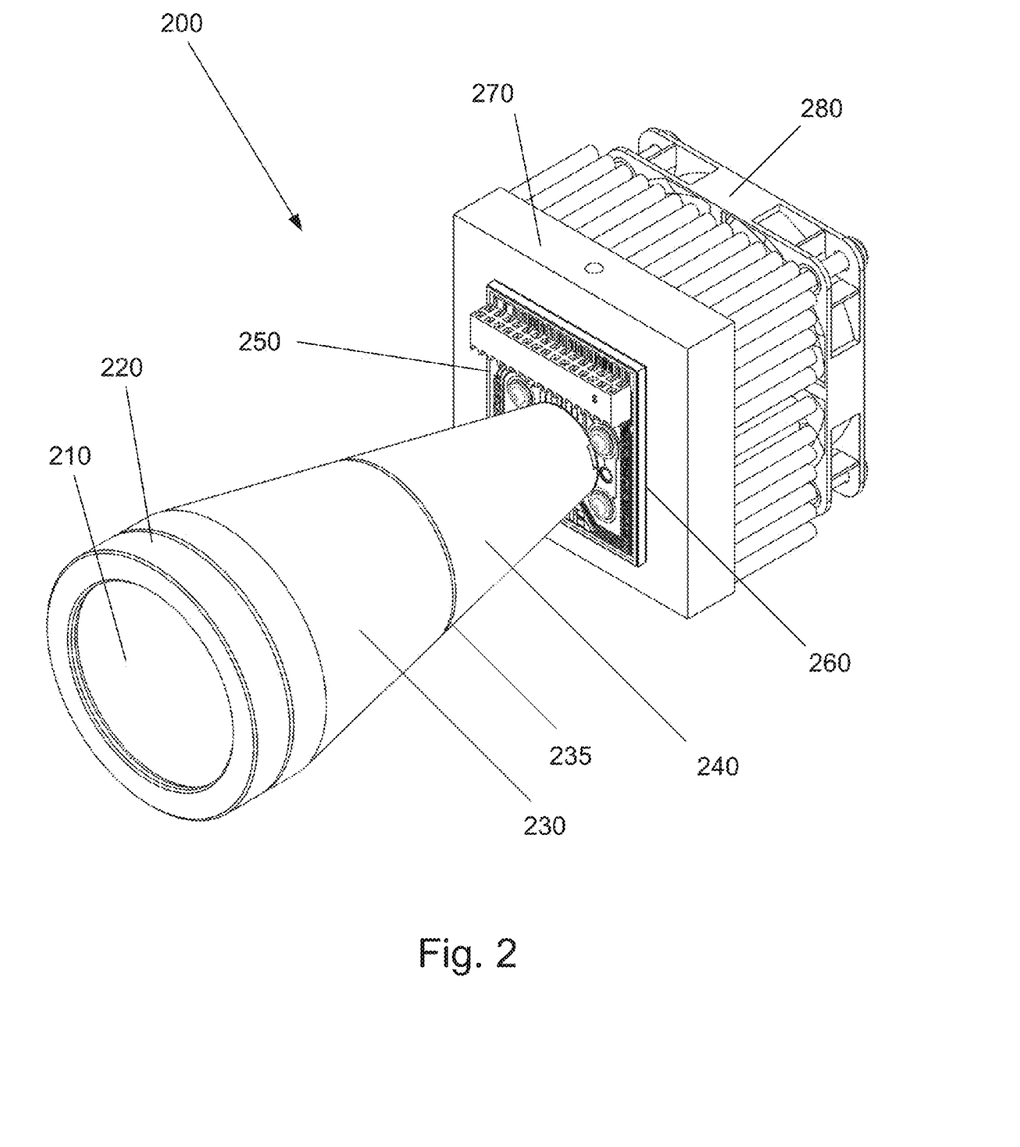
FIG. 2 shows an enlarged diagrammatic isometric view of part of the preferred embodiment of FIG. 1.

FIG. 1 shows an isometric view of a preferred embodiment of the light emitting diode (LED) projection system 100 comprising a projector 200, a set of emitted rays 120, and an illumination plane 110. FIG. 2 shows an enlarged isometric view of the projector 200 of FIG. 1. An LED board 250 is thermally attached to a heat sink 270 and a cooling fan 280 by a thermally conductive pad 260. The thermal pad 260 is typically thin, on the order of a quarter of a millimeter, and can be either electrically conductive or electrically neutral but generally of low thermal impedance. Materials for the thermal pad 260 are available from companies such as The Bergquist Company, of Chanhassen, Minn. They are available in a range of thicknesses, thermal impedances, electrical conductivity, and material compliance. Alternatively, a thermally conductive paste can replace the thermal pad 260, but pastes can be awkward in volume production and are not generally preferred.

The LED board 250 is based on "Chip on Board" (COB) technology for which LED die and other auxiliary components are attached directly to the metal core board via solder or thermally conductive epoxy. Generally, solder is preferred due to its lower thermal impedance, but some LED die are not available with a bottom contact that can be soldered, so under such circumstances, a thin layer of silver or diamond filled thermally conductive epoxy can be used instead. The LED board 250 is attached on top to a system of optics contained in a housing section 240. Housing section 240 contains a collection optic 460 (See FIG. 4), and a second housing section 230. contains re-imaging optics discussed more fully hereinafter but shown generally in FIG. 4 as well. A distal optical element 210 is held in place by a retainer 220 which threads onto the end of the section 230. The interface between housing the sections 230 and 240 represents a focusing mechanism 235 which allows the focus to be adjusted by moving the imaging optics relative to the output aperture of the collection optic via rotating threads in the two mating housing sections. Alternatively, the reimaging optics could comprise a zoom lens system to allow for changes in the magnification of the output face of the collection optic onto the illumination plane.

Figure 3:
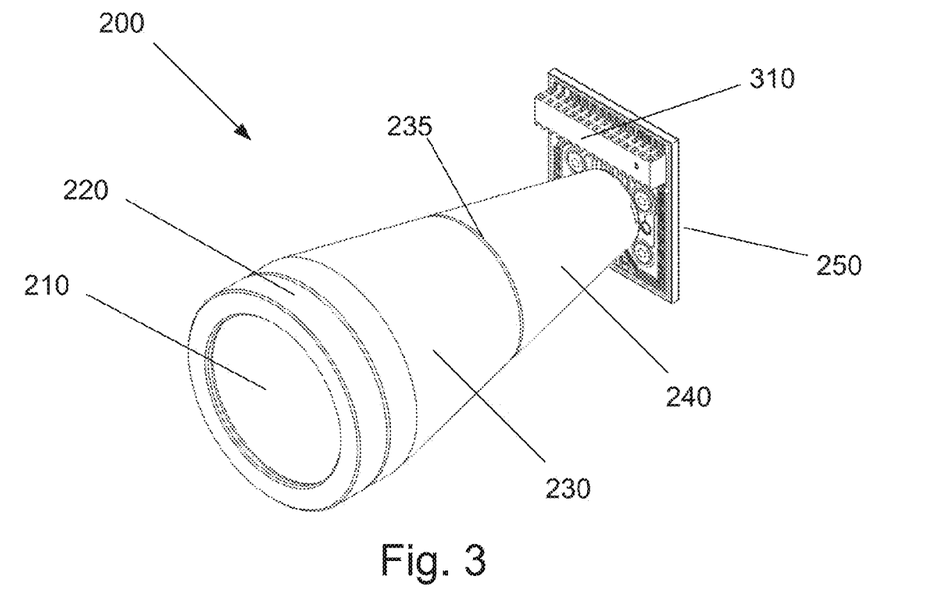
FIG. 3 is an isometric view of the embodiment of FIG. 2 with the heat sink and fan removed.

FIG. 3 shows a close up isometric view of the projector 200 of FIG. 2 without the heat sink 270 and the fan 280 attached. The LED 640 (See FIG. 6) is powered and controlled through contacts on a connector 310.

Figure 4:
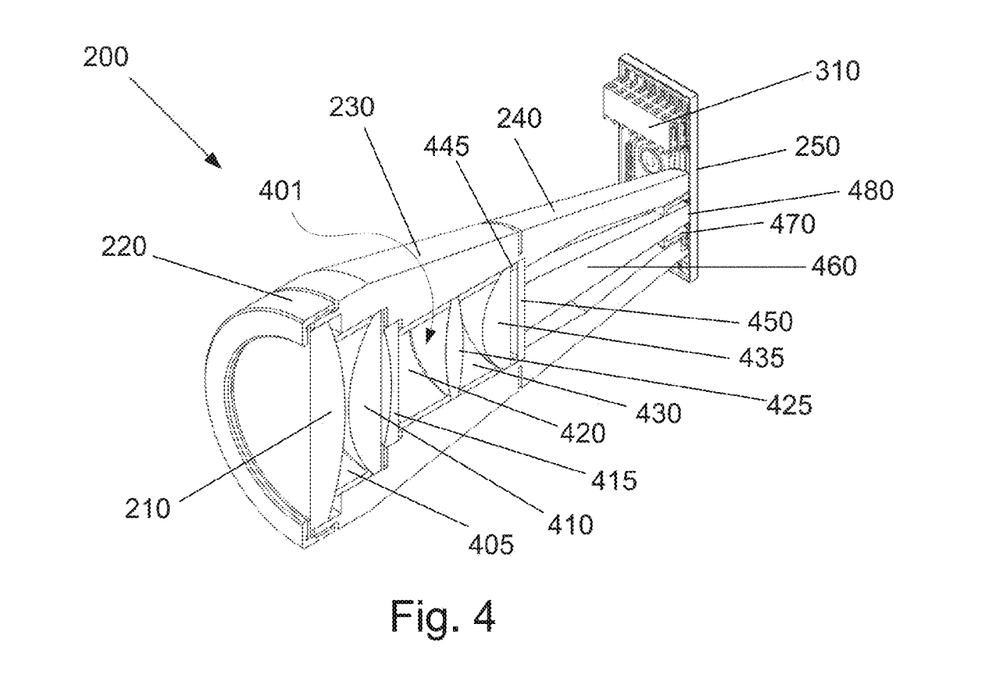
FIG. 4 shows a cross sectional view of the system of FIG. 3 indicating the internal optical components and mechical hardware.

FIG. 4 shows an isometric cross sectional view of the projector 200 of FIG. 3 showing its internal optical components. The emission from the LED die or die array 640 attached to the board 250 is efficiently collected by a non-imaging collection optic 460 at an input aperture 480 thereof. The radiant energy emitted by the LED die is efficiently and substantially collected by the non-imaging collection optic 460 and directed thereby to its exit aperture 710 (See FIG. 7) that is coincident with a window 450. The output of any single point of emission on the LED die or die array is substantially homogenized by the non-imaging collection optic 460 such that the near field intensity distribution at the collection optic's output aperture, preferably rectangular, is highly uniform. A re-imaging system of lenses generally shown at 401 and comprising a lens 435 (positive), lens 425 (positive), lens 415 (negative), lens 410 (positive), and lens 210 (positive), respectively, maps the near field output of the non-imaging collection optic 460 to the illumination plane 110 of FIG. 1. A set of spacers 445, 430, 420, and 405 separate the lenses 435, 425, 415, 410, and 210, respectively. The system of lenses is housed in the housing element 230 which, moves axially relative to the housing section 240 to adjust the focus by means of rotating threads at the interface between the housing sections 230 and 240. A collection optic holder 470 aligns to kinematic features in the board 250 to assure precise positional alignment between the LED array and the collection optic 460.

Figure 5:
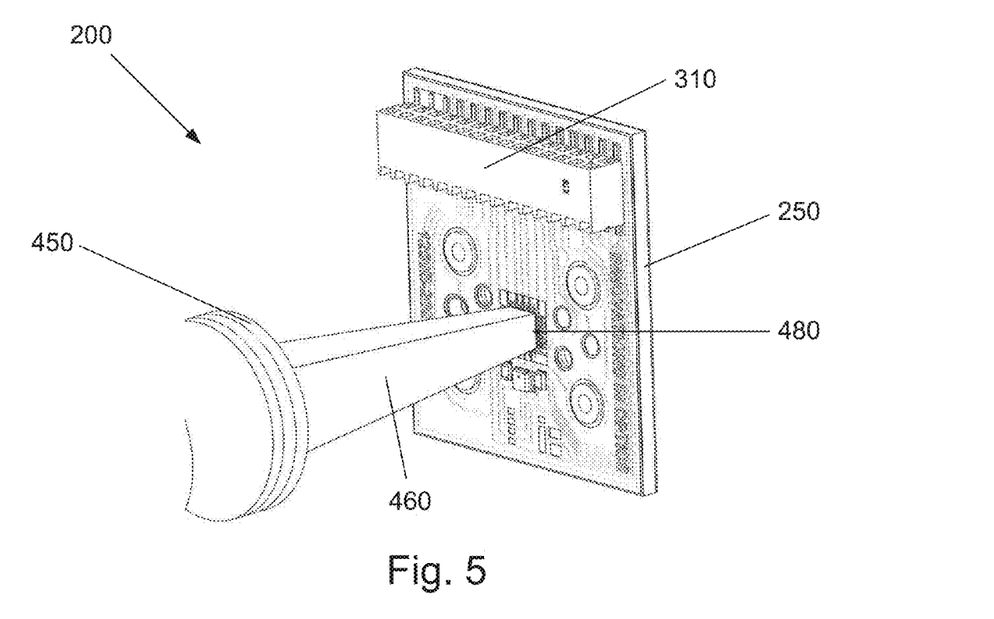
FIG. 5 shows a close up view of the system of FIG. 3 with the housing removed to show the interface between the LEDs and collection optic.
Figure 6:
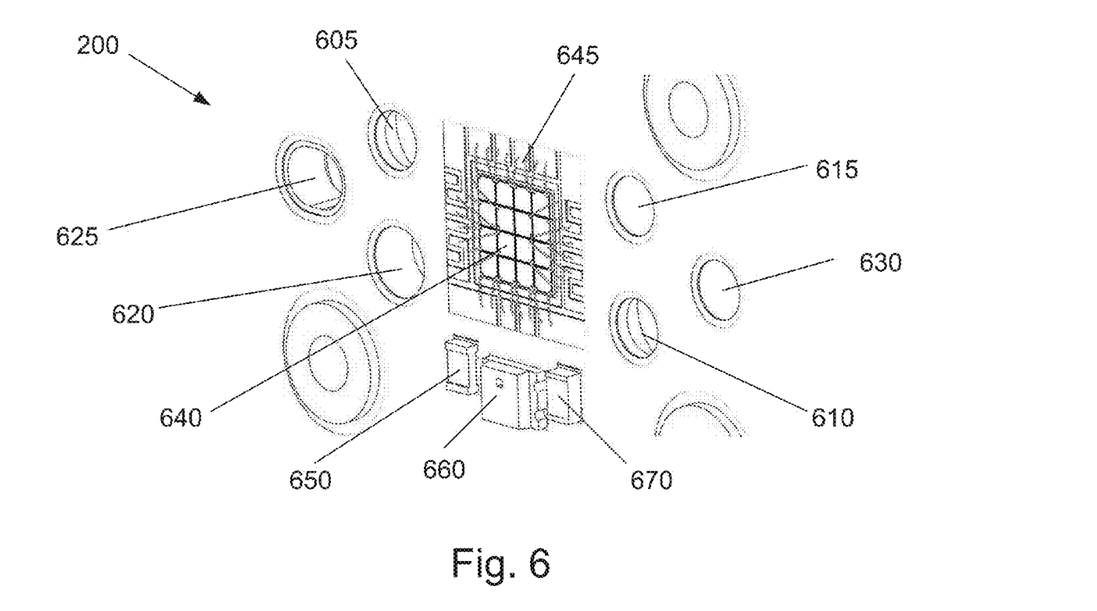
FIG. 6 shows an enlarged view of the system of FIG. 5 with the optics removed to show the LEDs, photosensor, and temperature measuring thermistor.

FIG. 5 shows an enlarged isometric view of the projector 200 of FIG. 3 shown with parts broken away. As such, FIG. 5 shows a close up view of the collection optic 460 with the input aperture 480 and output aperture contacting the window element 450. The input aperture 480 is shown in close proximity to LED array 640 (See FIG. 6) on the LED board 250. The square input aperture of the 4 by 4 die array is positioned on the order of 150 microns from the LED die to assure substantial collection efficiency of 90% or greater. The wire bonds are wedge type to assure minimal space is required. FIG. 6 shows a detailed isometric view of the LED board 250 and its attached surface mounted components. A slot 625 and a hole 630 comprise a set of kinematic mounting features that allow the board 250 to be precisely and repeatably attached to a thermal heat sink, if required for registration between the projector and object to be illuminated. A set of holes 605 and 610 are counter bored from the back side of the LED board 250 to allow screws to attach the board to the collection optic housing 240 shown in FIG. 3. A second set of holes 620 and 615 allow for a circular and oval pin in the back of the collection optic housing 240 to form a kinematic feature for precise alignment between the LED die array 640 and the non-imaging collection optic 460. These same two pins pass through and align the collection optic alignment component 470 of FIG. 4. A set of wedge type wire bonds 645 attach each LED die in the LED die array 640 to individual contacts on the LED board 250 which, in turn, run to individual contacts on the connector 310 of FIG. 5. Also shown in FIG. 6 is a photosensor 660, a photosensor feedback resistor 650, and a temperature sensing thermistor 670 that operate in a well-known manner to regulate or monitor temperature and LED output intensity.

There are benefits to both performance and cost for using COB metal core PCB's to directly attach the LED die or die arrays 640 relative to prior art, which typically use pre-packaged LED devices. The thermal impedance between LED die of the LED die array 640 and the heat sink 270 of FIG. 2 is much lower with the directly attached COB approach. Pre-packaged LED emitters have many additional layers of higher thermal impedance which means that, at high current densities, the COB system results in a much lower LED junction temperature, which leads to improved optical power and lower temperature operation which, in turn, translates into longer and more reliable product life. Additionally, fewer LED die can be used due to the higher performance for the COB approach, which further reduces system cost. The COB approach is also much lower in cost relative to the use of pre-packaged LED devices since there are fewer parts and fewer process steps to make a finished unit. The thermal performance advantage is particularly acute with respect to amber LED die with a photometric peak around 590 nm, as this LED material structure is much more sensitive to increased temperature which causes a drop in optical power. The thermal impedance with a COB LED solution can be as low as one (1) C.°/W, or lower, in comparison to typical values on the order of eight (8) to ten (10) C.°/W for pre-packaged devices. Examples of pre-packaged devices include the Luxeon™ and Rebel™ product lines now sold by Philips, the Osram Dragon™ and Oster™ product lines, and the CREE X-Lamp™ product line. There are now several vendors producing COB metal core LED boards such as those available from The Bergquist Company of Chanhassen, Minn. The lowest thermal impedance is obtained by mounting the LED die array 640 directly to the metal core boards which are typically copper or aluminum substrates However, that approach requires that the LED die have common anodes (bottom contact). Other high performance board substrates include, but are not limited to, composite materials such as aluminum, or copper and silicon carbide, graphite or CVD diamond, or more recently vapor chambers, which are a type of heat pipe working in two rather than one dimension. Additionally, it is generally not possible to obtain prepackaged devices that allow a close packed array to obtain the highest possible optical power densities as compared to the system 200 of FIG. 6, or to mix different LED spectral bands in such close proximity.

An additional benefit of using COB PCB technology is that electrical drive circuit devices and monitoring circuit devices can be attached directly to the COB PCB by standard surface mounting techniques well-known in the art thereby eliminating the need for the added cost, space, and complexity of additional external circuitry. Additional LED drive components can also be attached to the board representing even greater system level value. A wire harness or electrical connector can be mounted directly to the COB PCB connector 310 to get power and or control signals to and from the board 250 of FIG. 5. A temperature sensing device such as the thermistor 670 (See FIG. 6) can be added to the COB PCB to monitor temperature. If closed loop intensity operation is required, a light detection and control circuit such as the photosensor 660 and the photosensor feedback resistor 650 are attached, as shown, to the COB PCB board 250 to account for changes in light output from the LED die array 640 as a function of time and temperature. COB PCB's can have multiple layers attached by standard electrical vias with successive foil layers separated by thin thermally conductive dielectric layers on the order of 75 microns to allow for even more complex surface mounted circuit configurations. Standard foil thicknesses are available from 1 to 10 oz.

Figure 7:
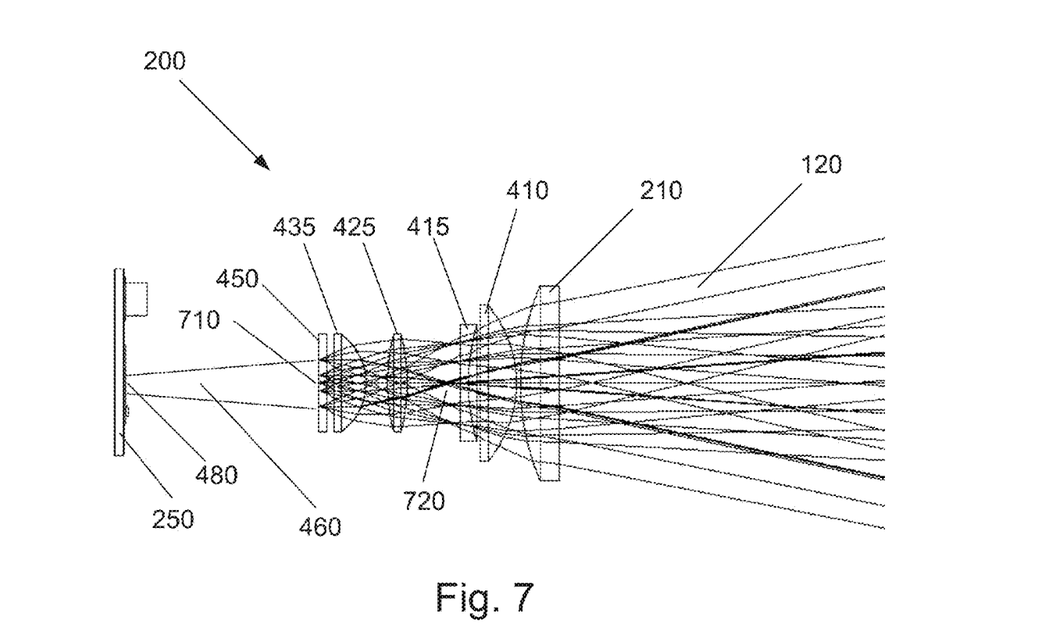
FIG. 7 shows a side view of the system of FIG. 4 indicating how the rays propagate from the LEDs through the collection optic and then are reimaged by a system of lenses.

FIG. 7 shows a cross sectional view of the projector LED board 250 and optics of the projector 200 of FIG. 3. Light is emitted from the LED die array 640 of FIG. 6 on the LED board 250 into the collection optic input aperture 480 of non-imaging collection optic 460. The ratio of input aperture size to output aperture size, and length of the collection optic 460, which is tapered in both axes, is optimized to result in a highly uniform near field intensity distribution at an exit aperture 710 of the collection optic 460 and to transform the far field extent from $2\pi$ down to a smaller value corresponding to a numerical aperture (sine of the half angle of emittance, designated by "NA")) on the order of NA 0.50, which is more manageable for the lens re-imaging system 401. One important property of the collection optic 460 is its ability to homogenize the output such that any one point, or individual LED die, at the input is substantially mixed spatially at the exit aperture 710. This allows the output of a single LED die to fully and uniformly fill the illumination pattern at the illumination plane 110 of FIG. 1. The trade off for the collection optic 460 is length versus degree of uniformity for a point input with a Lambertian (uniform $2\pi$ source with cosine fall off in intensity with angle) and the extent and uniformity of the far field. The longer the optic relative to its input and output dimensions, the better the uniformity, in general. For most practical and cost effective systems, however, it is not acceptable to make the length of the collection optic 460 too long as the overall length of the system would be unacceptable, and the cost would be increased, relative to that of a shorter optic. For most applications, a uniformity on the order of 1% is more than acceptable as these illumination systems are generally used with camera systems that can correct for some level of non-uniformity. One disadvantage of having too much intensity variation is that the imaging camera system has a finite bit resolution and the more that is taken up by compensating for intensity variations, the less dynamic range that is available for image capture, which ultimately limits system level sensitivity.

With reference to FIG. 7, the emission from the LEDs 640 into the collection optic input aperture 480 is spatially homogenized or mixed as it propagates to the output of the collection optic at rectangular output aperture 710. The set of rays 120 (e.g, FIG. 1) is shown to start at the output aperture 710 of the collection optic 460 which, in turn, are imaged through the window 450, which acts to hold the collection optic 460 in place, and then through the set of imaging lenses 435, 425, 415, 410, and 210, respectively. The rays can be seen forming an image of the stop at a plane 720. If desired, a stop could be added of any arbitrary shape at this point to control the angular extent of the far field distribution. The lens system shown here is corrected in a well-known manner for wavelength by an appropriate combination of lens material dispersions, lens curvatures, thicknesses, and spacing. The lenses can be made of a variety of materials including glass, plastic, silicone, or various optical crystalline materials well-known in the art. Additionally, the number of lens elements can be reduced by introducing aspheric optical elements. It is important to note, however, that if the LED output includes ultraviolet, the materials should be selected to have minimal yellowing with exposure to UV, low UV absorption as not to attenuate too much signal, and low fluorescence for applications of fluorescence imaging.

Figure 8:
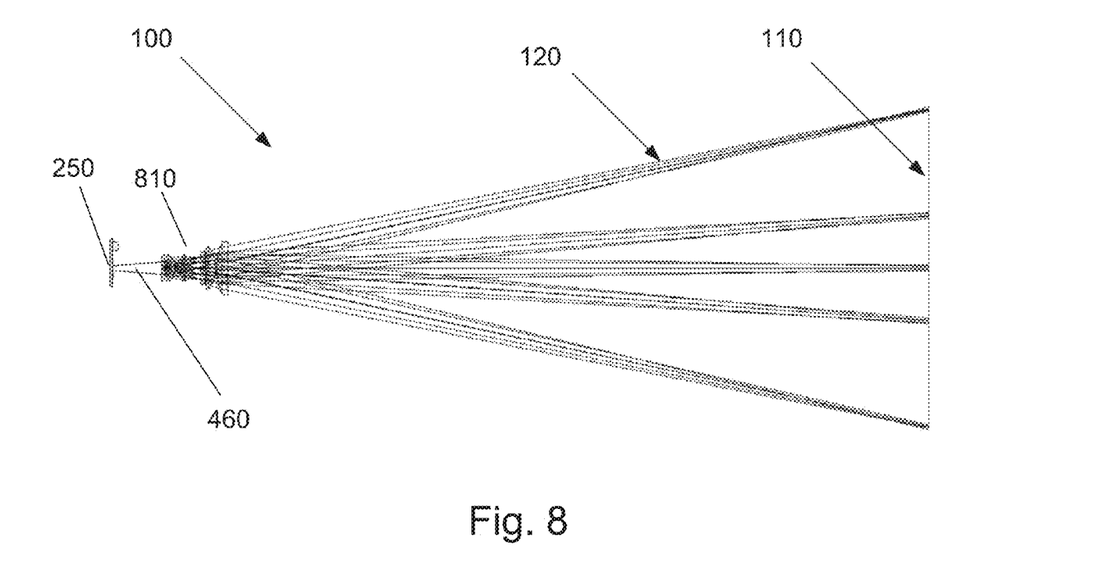
FIG. 8 shows the system of FIG. 7 showing how the rays propagate to the illumination plane, which is conjugate to the exit aperture of the collection optic.

FIG. 8 shows a cross sectional view of the system 100 of FIG. 1 with the heat sink 270 and the fan assembly 280 not shown. The rays 120 are shown to continue to the illumination plane 110. The system of lenses 401 maps the near field output of non-imaging collection optic 460 at the output aperture 710 to the illumination plane 110, which is generally in the far field, depending on image conjugates. Thus, the far field uniformity emitted at the output aperture 710 of the collection optic 460 of FIG. 7 is not important in producing the highly uniform intensity distribution at the illumination plane 110 of the system 100; it is really only a function of the near field uniformity at the output aperture 710, except for the requirement that all the light emitting at the output aperture 710 needs to be transmitted without vignetting by the optical system 401. It is important to note that any imperfections on the window 450 or the output aperture 710 would be imaged to the illumination plane 110, so care is required in keeping these surfaces free of defects and debris. An index matching gel or optical adhesive can be added between the aperture 710 and input side of the window 450 if desired and would eliminate the need to anti-reflection coat the optics to reduce Fresnel reflection losses at the collection optic output and front surface of the window.

Figure 9:
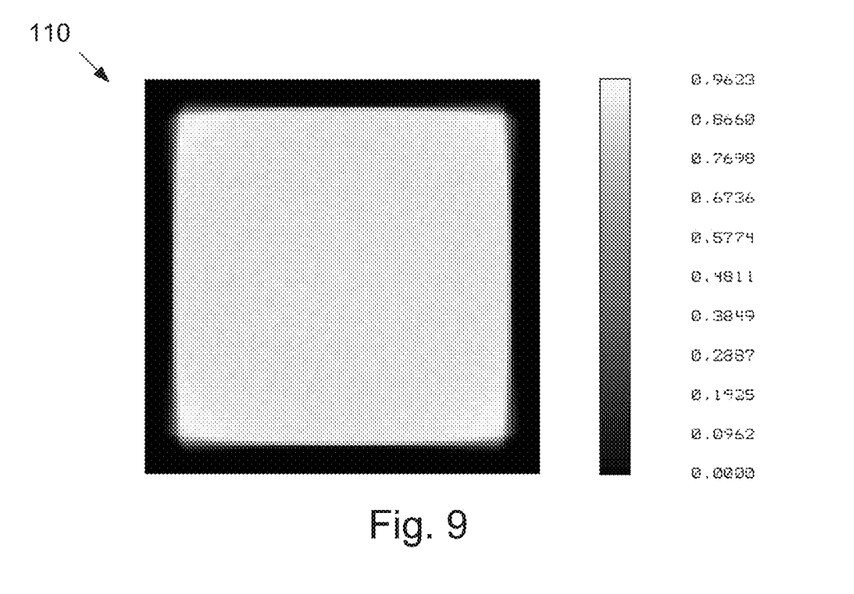
FIG. 9 shows a gray scale image at the illumination plane of the system of FIG. 8.

FIG. 9 shows a gray scale image of the illumination pattern that exists at the illumination plane 110 of the system 100. The output is substantially uniform to better than 1%. There is a slight amount of barrel distortion present, however, that has minimal affect on the intensity. In practice, it may be good to purposely build in a small degree of image blur to further homogenize any near field non-uniformities at the output of the collection optic 460 at the exit aperture 710. This can also blur out affects of small imperfections in the surface quality or finish of the optic elements 460 and 450 of the projector 200 of FIG. 7.

Figure 10:
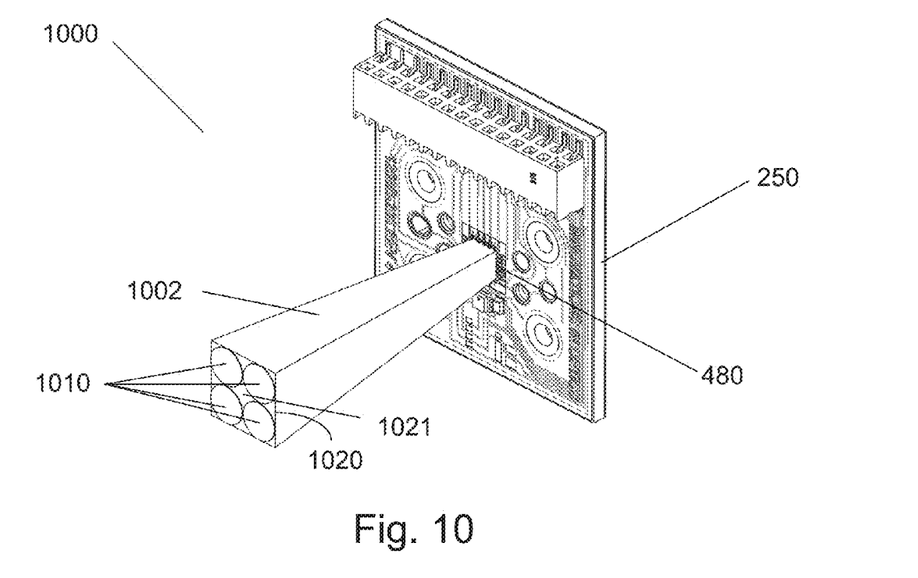
FIG. 10 shows an alternative output aperture of the system of FIG. 5 indicating an alternative output aperture including a reflective area surrounding four circular apertures.

FIG. 10 shows an isometric view of an alternative embodiment of the collection optic 460 of FIG. 5 shown in a system designated at 1000. Here, the collection optic designated at 1002 generally has a rectangular or square output with no secondary apertures on an output face 1020 of the collection optic 1002. In system 1000, however, the output face 1020 shows a set of circular apertures 1010 and an area 1021 representing the area not inside the circular apertures 1010. If, for example, the circular apertures 1010 are transparent, but the area 1021 is substantially reflective and not transmissive, then the LED emission that impinges on the transparent apertures 1010 is mapped in the same geometry, but magnified onto the illumination plane 110 of FIG. 1. The LED emission that impinges on the reflective aperture 1021, however, is directed back toward the LEDs, where it diffusely reflects off the LEDs and has an opportunity to pass back through the collection optic 1002 and map onto the illumination plane 110. In this way, it is possible to control of the geometric shape of the illumination on the illumination plane 110 by fabricating any arbitrary shape onto the output face of the collection optic 1002. Further, the intensity within the transparent aperture portions of the exit aperture 1020 of the collection optic 1002 is increased by virtue of this reflective mechanism.

Figure 11:
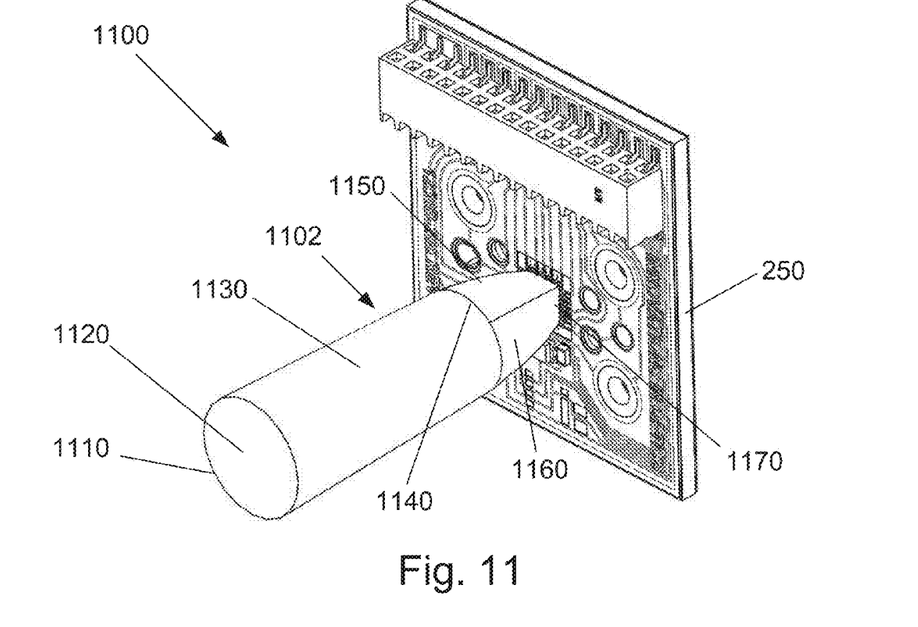
FIG. 11 shows an alternative collection optic to that of the system of FIG. 5 comprising a square input aperture and circular output aperture with a compound parabolic concentrator (CPC) profile.

FIG. 11 shows an isometric view of an alternative embodiment of the collection optic 1002 shown in the system 1000 of FIG. 10. Here, the collection optic is generally designated at 1102 in a system generally designated at 1100. The LED array 640 of the system 200 of FIG. 6 is shown in the system 1100 to interface to an input aperture 1170. Collection optic 1102 is a symmetric collection optic which transitions from a square input aperture 1170 to a circular aperture 1140. The input aperture 1140 comprises the input of a section 1130 that terminates distally in a circular exit aperture 1110 at an output surface 1120, which corresponds to the output aperture 710 of the collection optic 460 of the system 200 of FIG. 7. The side walls of the input of the collection optic 1102 of the system 1100 are comprised of a side section 1150 and a side section 1160, which have a substantially compound parabolic concentrator shape of the type described originally by Winston. The details of the shape will become clearer in the description below of FIG. 12.

Figure 12:
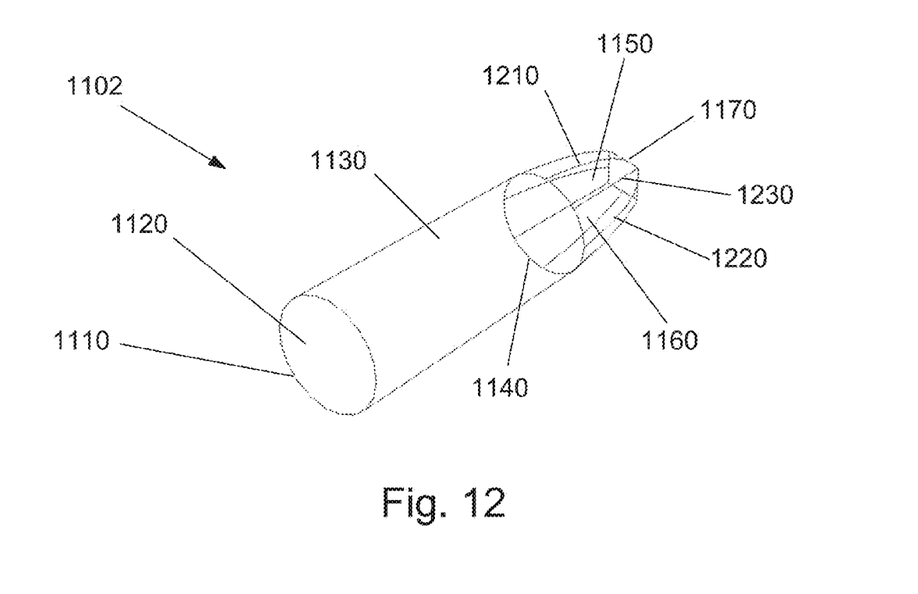
FIG. 12 shows a detailed view of the collection optic of the system of FIG. 11.

FIG. 12 shows a transparent isometric view of the collection optic 1102 of the system 1100. The input aperture 1170 is shown as rectangular and conforms to the shape of the LED array 640 of the projector 200 of FIG. 6. If an index matching material were used between the LED array and the input aperture 1170, then the shape of the collection optic 1102 of the system 1100 near its input aperture would be compound parabolic, but in the case of no index matching material, it would be a straight wall taper tangent to and changing to a section of a compound parabola. The center of each side of the collection optic 1102 would be described by a curve 1210 or a curve 1220 which is compound parabolic (in the case of index matching and tapered leading into a compound parabola in the case of no index matching) in contrast to the edges of the collection optic extending from the corners of the input aperture 1170 where the curve joins the square corners of the input aperture 1170 with the circular aperture 1140. The section 1130 acts to allow for further homogenizing of the distribution to achieve highly uniform emission in the near field at exit aperture 1110. It should be evident that the output of system 1100 can also be coupled to an optical fiber or fiber optic component of suitable NA rather than being used as part of an illumination projection system as initially described. The advantage of such a system which uses a rectangular input aperture to match to the rectangular dimensions of the LED die or die array in comparison to the use of a circular input aperture is the increased brightness of the output, which is useful in fiber optic illumination applications.

Figure 13:
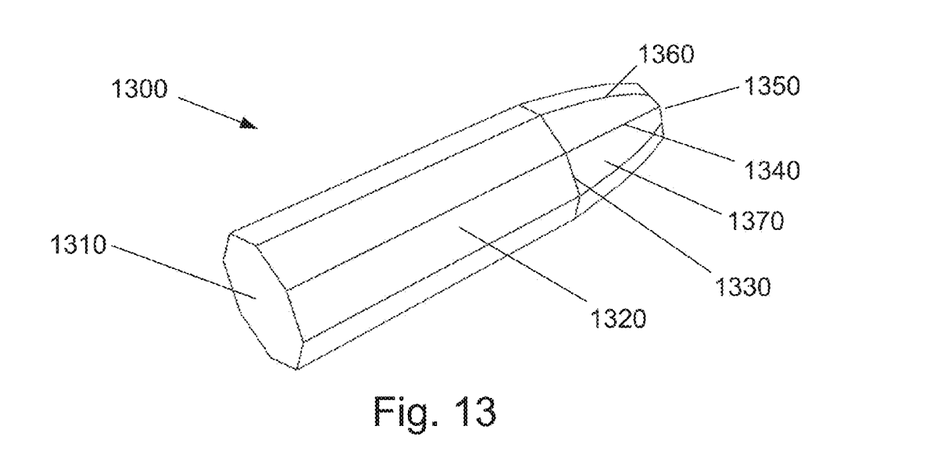
FIG. 13 shows an alternative optic to the optic of FIG. 12 which transitions from a square input aperture to an octogonal output aperture and homogenizing section.
Figure 14:
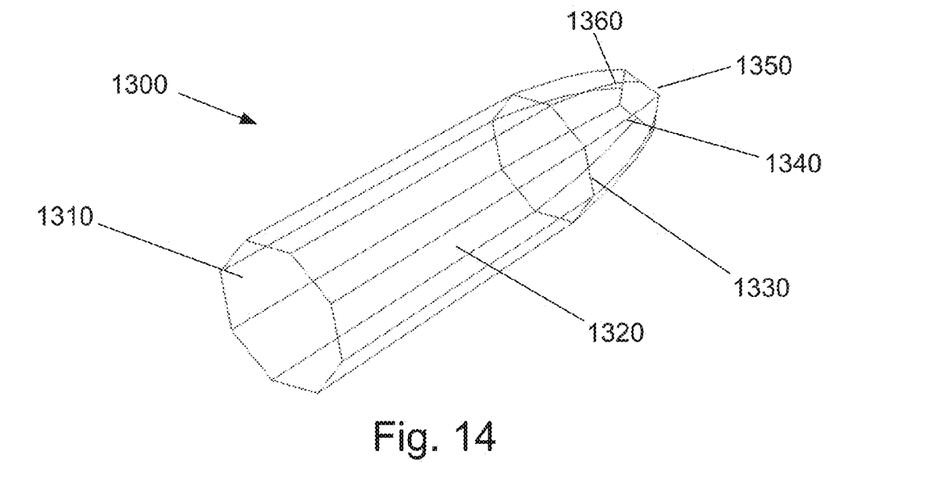
FIG. 14 shows the optic of FIG. 13 with hidden lines for a more detailed view.
Figure 15:
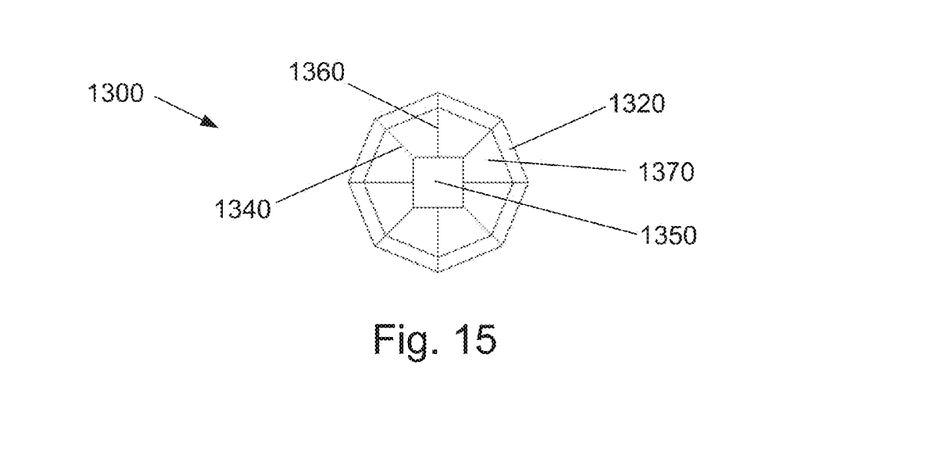
FIG. 15 shows an end on view of the optic of FIG. 13.

FIG. 13 represents an isometric view of an alternative embodiment to the collection optic of the invention and is designated as a system 1300. The difference between the collection optic of the system 1102 and that of the system 1300 is that the aperture 1140 of the system 1102 is replaced with an aperture 1330 that is octagonal. A section 1320 which extends from the aperture 1330 to an output aperture 1310 in the system 1300 replaces the section 1130 of the collection optic of the system 1102. The advantage of a light pipe with an even number of sides section 1320 is that it does a much better job of mixing the output of the LEDs in the near field at the output aperture of the collection optic and thus it can be shortened in length to achieve a specific degree of near field uniformity relative to that of the system 1102. An input aperture 1350 is rectangular similar to the input aperture 1170 of FIG. 12. A curve 1360 extends from the middle of each side of the input aperture 1350 to the vertex of the octagon at the aperture 1330 and is substantially compound parabolic for the index matched case and tapered to compound parabolic as described for the system 1102. The lines containing the planes intersecting the optical axis and the corners of the input aperture 1350 follow a best form merge in shape between the compound parabolic curves and the extremes of the sides representing the vertices of the apertures 1350 and 1330, respectively. Eight individual equally shaped sides represented by a side section 1370 represent the surface that transitions between the curves representing the middle of the sides of the input aperture 1350 by the curve 1360 and the curve 1340 joining the vertices of the two apertures 1350 and 1330. FIG. 14 shows an isometric view of the system 1300 of FIG. 13 with the sides transparent reveling all the far sides. FIG. 15 represents an end on view of the collection optic of the system 1300 of FIG. 13. It is evident from this end on view that there is a slight outward draft over the section 1320 between the apertures 1330 and 1310, which is not required in function, but is advantageous for releasing the part from the mold in the case of a molded plastic or glass optic.

Figure 16:
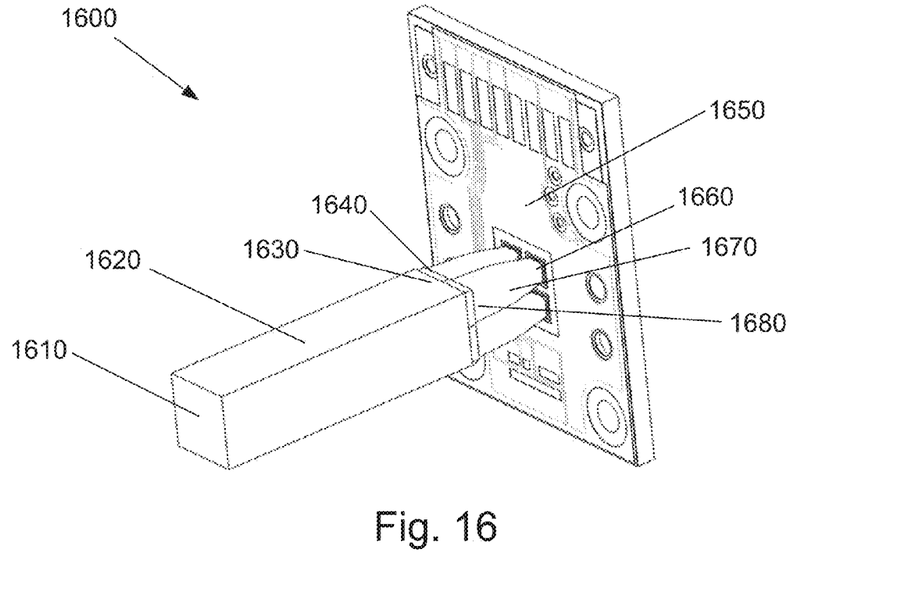
FIG. 16 shows an alternative embodiment to the system of FIG. 11 comprising an LED board with four groups of LED die with four independent collection optics with optical bandpass filters before entering into a homogenizer section that serves as a output aperture common to the four collection optics.
Figure 17:
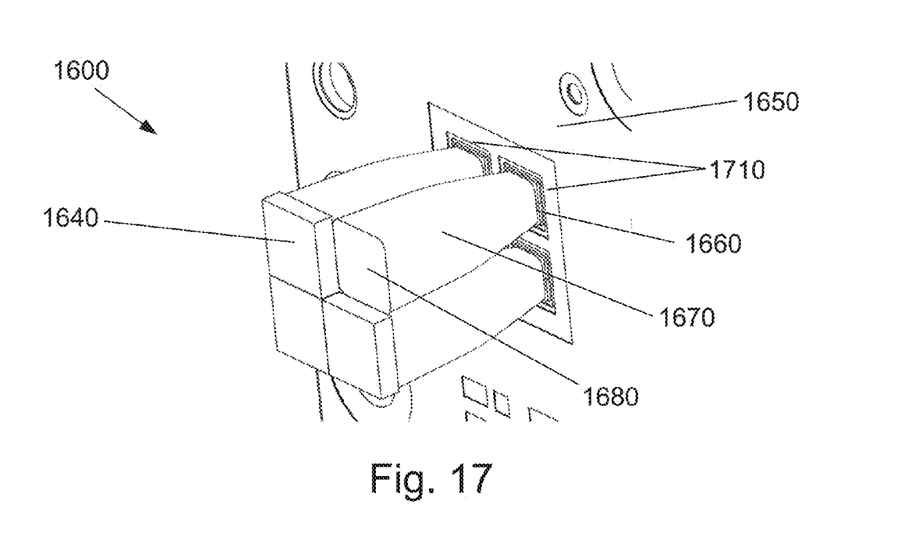
FIG. 17 shows a close up view of the system of FIG. 16 with the common homogenizer optic removed along with one of the bandpass filters to expose a view of the output aperture of one of the four collection optics.

FIG. 16 shows another alternative embodiment of the collection optic 460 of the invention and is designated by a system 1600. An LED COB board 1650 differs from the previous board 250 in that it comprises four independent and physically spaced LED arrays coincident with a set of four input apertures 1660 (typical) to a corresponding collection optic 1670 for each LED die or LED die array. Each of the collection optics 1670 would correspond to a different LED wavelength range. An output aperture 1680 of the collection optic 1670 would emit LED output through a set of spectral band limiting filters 1640 sandwiched between the output of the collection optics 1670 and a rectangular homogenizer 1620 with an input aperture 1630 and an output aperture 1610. FIG. 17 shows an isometric view of the system 1600 of FIG. 16 with the homogenizer 1620 and one of the filters 1640 removed for clarity. A set of LED die arrays 1710 comprised of one or more LED die would be grouped such that each input aperture corresponds to a different spectral band. In this way, a multi-spectral waveband LED source could be realized that allows for each spectral band to be turned on independently with high extinction on the long wavelength side of the band appropriate for fluorescence excitation applications. High extinction would also be preferred on the short wavelength side to prevent overlap in response between different fluorescing materials and to allow greater selectivity of response. The problem with using this type of projection system, which combines the spectral bands without attenuating the long wavelength side of each band, is that there would be unacceptably high residual LED intensity overlapping with the fluorescence emission bands. The output of each collection optic 1670 exits through the output aperture 1680 as indicated in the system 1600. The collection optic for this case, which is tapered, has a first section near the input aperture 1660, which transitions to a compound parabolic section near the middle of the optic 1670, and then transitions to a tapered section near the output aperture 1680. This allows the optic to be readily made by glass, plastic or silicone molding techniques. The side walls of each filter 1640 would be blackened to prevent cross talk between adjacent channels. This could be readily accomplished by providing a small gap between the output apertures 1680. It would also be preferred to blacken the sides of the filters or providing a baffle between the edges of the filters.

Figure 18:
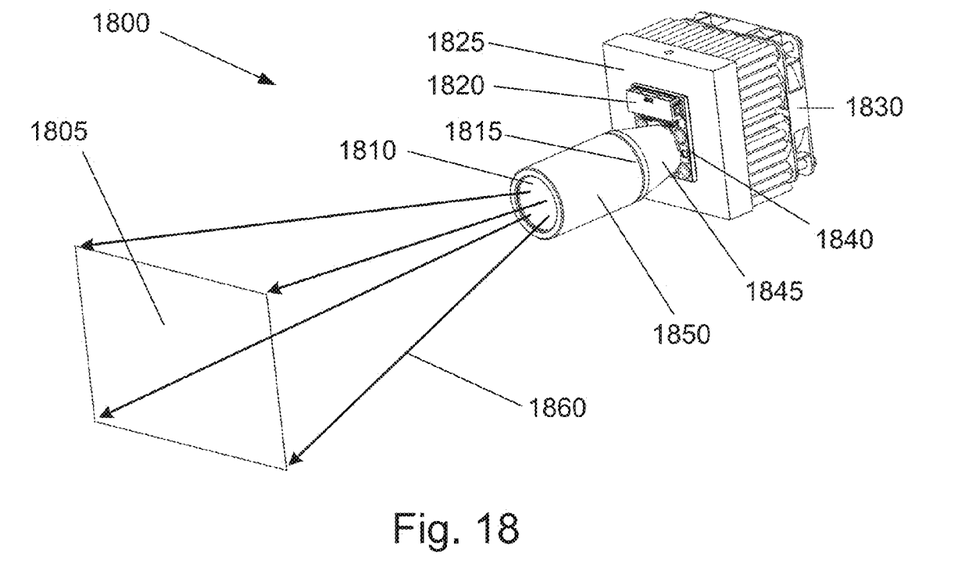
FIG. 18 shows an alternative embodiment to the embodiment of FIG. 1.
Figure 19:
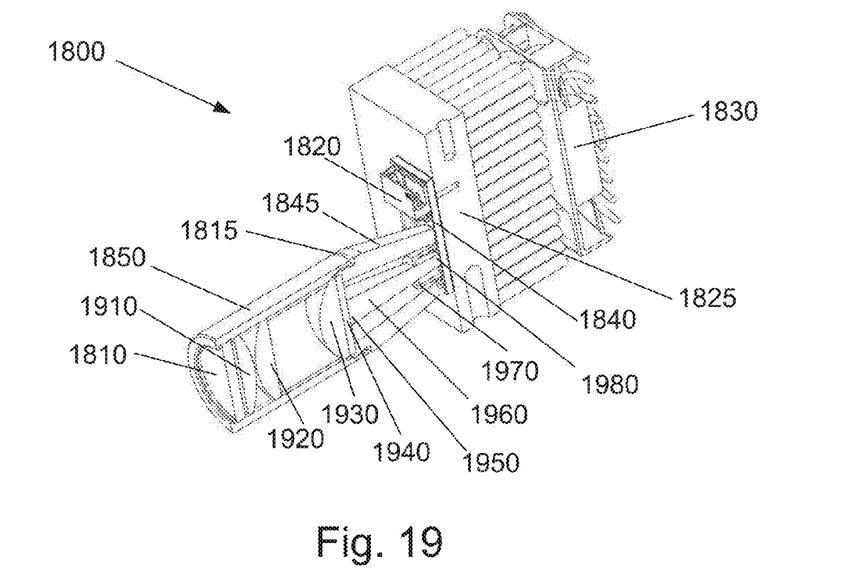
FIG. 19 shows a cross sectional view of the embodiment of FIG. 18.

FIG. 18 shows an isometric view of an alternative embodiment of a projector of the invention and is generally designated as a system 1800. A heat sink 1825 and a fan assembly 1830 are shown attached to an LED metal core COB board 1840. The LED module is powered by a connector 1820 attached to the LED board 1840. While the system 1800 could be used for any spectral band, it was designed specifically as a high uniformity and intensity source of ultraviolet LED emission. The housing is broken into a first section 1845 housing the collection optics and a second section 1850 housing the UV imaging optics and excitation filter. The UV power is emitted from an aperture 1810 designated by a set of rays 1860 incident on an illumination plane 1805. The interface between the optics housing sections 1845 and 1850 is designated by an area 1815 comprising a set of threaded mating parts to allow for focus adjustment if required. FIG. 19 shows an isometric cross sectional view of the system 1800.

The UV LED die array positioned in close proximity to input aperture 1980 and similar to LED array 640 of FIG. 6, is coincident with a collection optic 1960 at an input face 1980. The input aperture of this collection optic 1960 is square to interface with a square array of LED die on LED board 1840. However, the output aperture 1950 is rectangular to correspond to the rectangular illumination requirement for this UV tissue illumination system. Alternatively, the LED array could be rectangular as well, as long as the collection optic is shaped to capture substantially all the light emitted from the LED array. A collection optic holder 1970 is analogous in function to that of the holder 470 of the projector 200 of FIG. 4. The output of the collection optic 1960 is represented by output aperture 1950 which is coincident with a window 1940. A set of optics represented by a first lens 1930, a second lens 1920, and a third lens 1910 acts to image the near field output of aperture 1950 to the illumination plane 1805 of the system 1800 of FIG. 18. A filter 1810 comprises the distal element of the optic assembly. The advantage to placing the filter after the lens elements is that out of band auto-fluorescence of the lens elements would be substantially surpressed.

Figure 20:
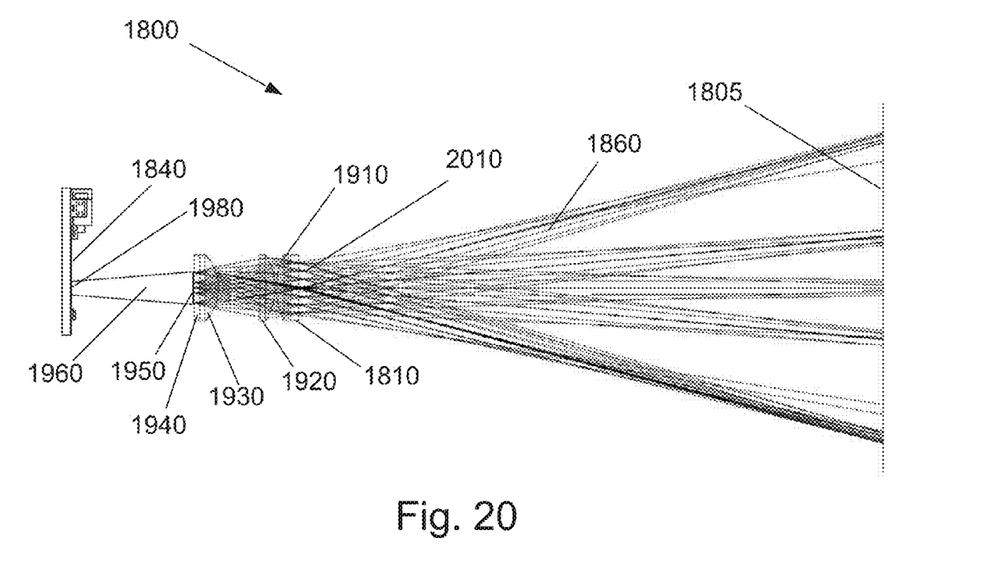
FIG. 20 shows a side view of the embodiment of FIG. 18 with optical rays shown between the output aperture of the collection optic and the illumination plane.
Figure 21:
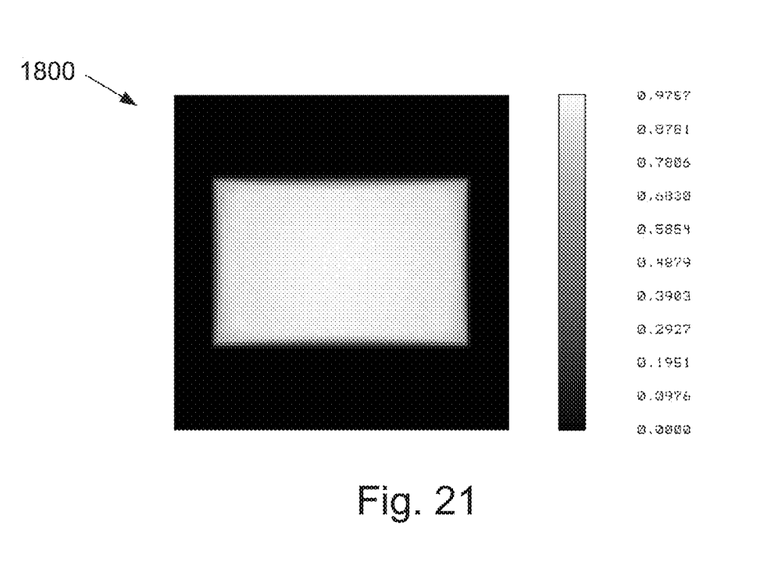
FIG. 21 shows a gray scale image of the intensity distribution of the embodiment of FIG. 18 showing the rectangular profile resulting from the similarly shaped collection optic output aperture.

FIG. 20 shows a cross sectional view of the system 1800 of FIG. 18 with the heat sink 1825 and the cooling fan assembly 1830 not shown. The rays 1860 are shown starting from the output aperture 1950 of the collection optic 1960 and extending through the window 1940, through the imaging lens elements 1930, 1920 and 1910, respectively, and then passing through the filter element 1810 to the illumination plane 1805. The rays 1860 are shown to form a pupil 2010 (an image of the stop) in the region coincident with the output from the filter 1810. If an absorption based filter, such as Schott Glass UG11, is used to cut off the small visible spectrum from the UV LEDs, then it can be positioned at the output element 1810 as indicated. If, however, it is required to use a multi-layered dielectric spectral fluorescence filter, then the filter would have an angular sensitivity, and it should instead be positioned in place of the window 1940, as it would have the same angular extent for all field positions at the output of the collection optic 1960 from the aperture 1950 due to the substantially telecentric output at aperture 1950. If, for example, an interference filter were positioned coincident with the filter position 1810, then the center of the illumination field 1805 would be different from the edges or extents of the field, which would not be desirable. FIG. 21 shows a gray scale image of the UV illumination field at the position of 1805 of system 1800. The shape is substantially rectangular, as was required for this application for illuminating a rectangular region of human tissue for a fluorescence imaging application. It should be evident to those schooled in the art and from the previous descriptions that any shape is feasible depending on the shape of the input LED array, the input and output shape and length of the collection optic and any transparent or opaque apertures at the collection optic output aperture 1950. The lighting non-imaging concentrators, for example, may have cross-sectional shapes selected from the group consisting of compound parabolic, compound elliptical, compound hyperbolic concentrators, straight tapers, and concentrators having curvatures described by higher order polynomial functions or combinations thereof with the exact shapes being determined using well-known ray tracing software.

Having described the invention with reference to specific embodiments, other variants will be apparent to those skilled in the relevant arts, and it is the intention that such variants be covered by the appended claims.

What is claimed is:

1. A lighting apparatus for providing area illumination of high uniformity and power density, said lighting apparatus comprising:
   a high thermal conductivity printed circuit board;
   at least one bare LED die comprising one or more LED emitting areas for generating radiation of one or more spectral bands over a predetermined solid angle, said at least one bare LED die being attached to said high thermal conductivity printed circuit board with a thermally conductive bonding layer;
   an electronic control module attached to said high thermal conductivity printed circuit board for controlling the output of said LED emitting areas;
   at least one non-imaging concentrator fixedly attached to and in registration with said high thermal conductivity printed circuit board, said non-imaging concentrator having entrance and exit apertures, said non-imaging concentrator entrance aperture being optically aligned with said LED emitting areas for collecting radiation from said LED emitting areas and re-emitting it through said non-imaging concentrator exit aperture with an étendue substantially the same as that of said LED emitting areas, said non-imaging concentrator operating to homogenize the LED output to provide at the non-imaging collection optics exit aperture a high degree of near field intensity uniformity and a reduced far field extent substantially preserving the étendue of the LED output; and
   a relay lens for reimaging the near field of said non-imaging collector optics to an illumination plane a predetermined distance away from said non-imaging concentrator exit aperture.

2. The lighting apparatus of claim 1 further including a photosensor attached to said high thermal conductivity printed circuit board at a predetermined spaced apart location with respect to said LED die for providing a feedback signal to said electronic control module to regulate the output of said LED emitting areas.

3. The lighting apparatus of claim 1 wherein said non-imaging concentrator re-emits substantially all of the radiation collected thereby as a diverging beam having a solid angle smaller than said predetermined solid angle over which radiation is emitted by each of said LED emitting areas.

4. The lighting apparatus of claim 1 further including a heat sink thermally bonded to said high thermal conductivity printed circuit board on the side opposite to that on which other components are attached to selectively dissipate heat generated in the process of converting electrical energy to optical power to enhance the quantum efficiency of said lighting apparatus.

5. The lighting apparatus of claim 1 further including a thermistor mounted on said high thermal conductivity printed circuit board to monitor temperature and provide a feedback signal to said electronic control to assist in regulating the operating temperature of said apparatus and the output of said LED emitting areas.

6. The lighting apparatus of claim 1 wherein said at least one bare LED die comprises an array of regularly spaced LED die and an array of spaced apart non-imaging concentrators the individual non-imaging concentrators of which are also regularly spaced and optically coupled in one-to-one correspondence with said regularly spaced LED die.

7. The lighting apparatus of claim 6 wherein at least one of the LED dies of said array has a spectral output that differs from the other LED dies of the array.

8. The lighting apparatus of claim 7 further including a homogenizing section located downstream of said non-imaging concentrator exit aperture to promote uniform color and intensity distribution in said apparatus output.

9. The lighting apparatus of claim 8 wherein the spectal outputs of all of the LED die of said array differ from one another.

10. The lighting apparatus of claim 6 wherein said array comprises at least a one by two matrix the elements of which comprise at least a one by two matrix of LED emitting areas.

11. The lighting apparatus of claim 1 wherein said spectral bands of said LED emitting areas range from the ultra violet to near to mid infrared.

12. The lighting apparatus of claim 1 wherein said non-imaging concentrators have cross sectional shapes that differ along their length.

13. The lighting apparatus of claim 12 wherein said different cross sectional shapes of laid non-imaging concentrators are selected from the group comprising squares, rectangles, circles, and polygons.

14. The lighting apparatus of claim 1 wherein said non-imaging concentrators have cross-sectional shapes selected from the group consisting of compound parabolic, compound elliptical, compound hyperbolic concentrators, straight tapers, and concentrators having curvatures described by higher order polynomial functions or combinations thereof.

15. The lighting apparatus of claim 1 further including a homogenizing section located downstream of said non-imaging concentrator exit aperture to promote uniform color and intensity distribution in said apparatus output.

16. The lighting apparatus of claim 15 wherein said homogenizing section has a cross-section shape selected from the group comprising squares, rectangles, circles, and polygons.

17. The lighting apparatus of claim 12 wherein said non-imaging concentrators are rectangular in cross section to control the divergence of said diverging beam in vertical and horizontal planes mutually perpendicular to said optical axis.

18. The lighting apparatus of claim 1 wherein said non-imaging concentrator is fabricated of a material selected from the group consisting of optical plastic, molded glass, ground glass, polished glass, and silicone.

19. The lighting apparatus of claim 1 wherein said exit aperture of said non-imaging concentrator comprises transparent apertures and reflective surfaces interspersed between said transparent apertures where said reflective surfaces intercept radiation that does not directly pass through said transparent apertures from said LED emitting areas and direct it back toward said LED emitting areas to be reflected therefrom through said transparent apertures to increase the light coupled out of said exit aperture over that which would be achieved without the use of said reflective surfaces.

20. The lighting apparatus of claim 1 wherein said non-imaging concentrator has a cross-sectional shape that transitions between a rectangular input aperture and a circular output aperture.

21. The lighting apparatus of claim 1 wherein said non-imaging concentrator has a cross-sectional shape that is rectangular.

22. The lighting apparatus of claim 1 wherein said non-imaging concentrator comprises a first housing section for supporting said non-imaging concentrator and an optic housing section for supporting said relay lens, said first housing section having locating pins that fit into complementary configured holes in said high thermal conductivity printed circuit board to locate said non-imaging concentrator with respect to said high thermal conductivity printed circuit board.

23. The lighting apparatus of claim 22 wherein said first housing section and said optic housing section are moveable with respect to one another to adjust the focus of said relay lens.

24. The lighting apparatus of claim 1 wherein said relay lens comprises a multi-element lens whose focus is adjustable to image said far field.

25. A lighting apparatus for use with optical fibers, said lighting apparatus comprising:
  a high thermal conductivity printed circuit board;
  at least one bare LED die comprising one or more LED emitting areas for generating radiation of one or more spectral bands over a predetermined solid angle, said at least one bare LED die being attached to said high thermal conductivity printed circuit board with a thermally conductive bonding layer;
  an electronic control module attached to said high thermal conductivity printed circuit board for controlling the output of said LED emitting areas; and
  at least one non-imaging concentrator fixedly attached to and in registration with said high thermal conductivity printed circuit board, said non-imaging concentrator having a square entrance aperture and a circular exit aperture, said non-imaging concentrator entrance aperture being optically aligned with said LED emitting areas for collecting radiation from said LED emitting areas and re-emitting it through said non-imaging concentrator exit aperture with a predetermined étendue to match that of a downstream fiber optic.

\* \* \* \* \*